United States Patent [19]
Okada et al.

[11] Patent Number: 5,814,342
[45] Date of Patent: *Sep. 29, 1998

[54] PROLONGED RELEASE MICROCAPSULES

[75] Inventors: Hiroaki Okada, Suita; Yayoi Inoue, Kyoto; Yasuaki Ogawa, Otokuni-gun, all of Japan

[73] Assignee: Takeda Chemical Industries, Ltd., Osaka, Japan

[*] Notice: The term of this patent shall not extend beyond the expiration date of Pat. Nos. 5,480,656 and 5,643,607.

[21] Appl. No.: 806,954

[22] Filed: Feb. 26, 1997

Related U.S. Application Data

[62] Division of Ser. No. 458,679, Jun. 2, 1995, Pat. No. 5,643,607, which is a division of Ser. No. 188,918, Jan. 31, 1994, Pat. No. 5,480,656, which is a continuation of Ser. No. 649,727, Feb. 1, 1991, abandoned.

[30] Foreign Application Priority Data

Feb. 13, 1990 [JP] Japan ..................................... 2-33133

[51] Int. Cl.[6] .............................. A61K 9/52; A61K 9/62
[52] U.S. Cl. .......................... 424/493; 424/461; 424/489; 514/2; 514/3; 514/16; 514/20; 514/937
[58] Field of Search ..................... 424/426, 455, 424/457, 491, 493, 489; 514/2, 3, 16, 20, 937

[56] References Cited

U.S. PATENT DOCUMENTS

| | | | |
|---|---|---|---|
| 4,001,388 | 1/1977 | Shell | 424/490 |
| 4,532,123 | 7/1985 | Gardner | 428/402.21 |
| 4,637,905 | 1/1987 | Gardner | 264/4.3 |
| 4,652,441 | 3/1987 | Okada et al. | 424/19 |
| 4,711,782 | 12/1987 | Okada et al. | 424/455 |
| 4,728,721 | 3/1988 | Yamamoto et al. | 528/361 |
| 4,761,398 | 8/1988 | Edens et al. | 514/21 |
| 4,849,228 | 7/1989 | Yamamoto et al. | 424/457 |
| 4,895,724 | 1/1990 | Cardinal et al. | 424/489 |
| 4,897,268 | 1/1990 | Tice et al. | 424/489 |
| 4,917,893 | 4/1990 | Okada et al. | 424/423 |
| 4,954,298 | 9/1990 | Yamamoto et al. | 424/457 |
| 5,028,430 | 7/1991 | Sanders et al. | 514/15 |
| 5,102,872 | 4/1992 | Singh et al. | 514/21 |
| 5,227,157 | 7/1993 | McGinity et al. | 424/441 |
| 5,271,945 | 12/1993 | Yoshioka et al. | 424/489 |
| 5,480,656 | 1/1996 | Okada et al. | 424/493 |
| 5,643,607 | 7/1997 | Okada et al. | 424/493 |

FOREIGN PATENT DOCUMENTS

| | | |
|---|---|---|
| 0 052 510 | 5/1982 | European Pat. Off. . |
| 0 145 240 | 6/1985 | European Pat. Off. . |
| 0 190 833 | 8/1986 | European Pat. Off. . |
| 0 202 065 | 11/1986 | European Pat. Off. . |
| 0 256 726 | 2/1988 | European Pat. Off. . |
| 0 350 246 | 1/1990 | European Pat. Off. . |
| 60-100516 | 6/1986 | Japan . |
| 63-41416 | 2/1988 | Japan . |

OTHER PUBLICATIONS

Sanders et al., "Controlled Release of a Luteinizing Hormone–Releasing Hormone Analogue From Poly(d,l–lactide–co–glycolide) Microspheres", *Journal of Pharmaceutical Sciences*, vol. 73, No. 9, pp. 1294–1297, (1984).

Reza–UI Jalil, "Biodegradable Poly(Lactic Acid) and Poly-(Lactide–co–glycolide) Polymers In Sustained Drug Delivery" *Drug Development and Industrial Pharmacy*, vol. 16(16), pp. 2353–2367, (1990).

*Primary Examiner*—Gary L. Kunz
*Attorney, Agent, or Firm*—Foley & Lardner

[57] ABSTRACT

This invention provides a microcapsule designed for zero order release of a physiologically active polypeptide over a period of at least two months, which is produced by preparing a water-in-oil emulsion comprising an inner aqueous layer containing about 20 to 70% (w/w) of said polypeptide and an oil layer containing a copolymer or homopolymer having a weight-average molecular weight of 7,000 to 30,000, wherein the composition ratio of lactic acid/glycolic acid in the copolymer or homopolymer is 80/10 to 100/0, and then subjecting said water-in oil emulsion to microencapsulation.

17 Claims, No Drawings ously active polypeptide over a period of at least two months, which is produced by preparing a water-in-oil emulsion comprising an inner aqueous phase containing about 20 to 70% (W/W) of said polypeptide and an oil phase containing a copolymer or homopolymer having a weight-average molecular weight of 7,000 to 30,000, the composition ratio of lactic acid/glycolic acid being 80/10 to 100/0, and then subjecting said water-in-oil emulsion to microencapsulation.

PROLONGED RELEASE MICROCAPSULES

This application is a division of application Ser. No. 08/458,679, filed Jun. 2, 1995, now U.S. Pat. No. 5,643,607, which is a divisional of application Ser. No. 08/188,918, filed Jan. 31, 1994, now U.S. Pat. No. 5,480,656, which is a continuation of application Ser. No. 07/649,727, filed Feb. 1, 1991, now abandoned.

FIELD OF THE INVENTION

This invention relates to microcapsules designed for sustained release of physiologically active peptide.

BACKGROUND OF THE INVENTION

Various dosage forms have been proposed for drugs required to be administered for a prolonged period. Among them, Japanese published unexamined patent application (Toku-Kai Sho) 57-118512 and its corresponding EP-A-0052510 disclose preparation of microcapsules by a phase separation method using a coacervation agent such as a mineral oil or a vegetable oil. Toku-Kai Sho 60-100516 (the corresponding U.S. Pat. Nos. 4652441 and 4711782), 62-201816 (the corresponding EP-A-0190833) and 63-41416 disclose methods of preparing microcapsules by means of in-water drying. According to these methods, drugs can be efficiently incorporated into microcapsules to give desirable microcapsules with less initial release.

In the case of administering a drug in the form of microcapsules, requirements for microcapsules having high dependency on interaction with functions of the living body are diversified into a variety of phases. Since the matter is concerned with medicines, microcapsules capable of satisfying those various requirements as far as possible have been desired.

There are many reports on microcapsules comprising a water-soluble drug using a biodegradable polymer. However, in the case of using a water-soluble drug, especially a physiologically active peptide having a relatively large molecular weight, the diffusion of the drug thus encapsulated into the polymer is low, and, therefore, the drug is not released at the initial stage until the decomposition or impregnating of the polymer proceeds. Also, as an adverse effect, a large burst at the initial stage cannot be avoided depending on the method of preparation. Thus it is often the case that practical difficulties occur with use as medicines. Especially, in sustained release pharmaceutical compositions over an extended period of time, constant release of the drug with higher accuracy is an important requirement, but no microcapsules satisfying those requirements have been known.

OBJECTS OF THE INVENTION

In view of these circumstances, the present inventors have conducted intensive studies with the purpose of developing pharmaceutical compositions designed for sustained release of a physiologically active peptide over an extended period of time. As a result, the present inventors found that, by preparing microcapsules using suitably selected polylactic acid of a limited molecular weight or lactic acid-glycolic acid (100/0 to 80/20), microcapsules having continuous excellent releasability for a long time were obtained. Further research work based on this finding has now led to completion of the present invention.

More specifically, the main object of the present invention is to provide a microcapsule designed for zero order release of a physiologically active polypeptide over a period of at least two months, which is produced by preparing a water-in-oil emulsion comprising an inner aqueous phase containing about 20 to 70% (W/W) of said polypeptide and an oil phase containing a copolymer or homopolymer having a weight-average molecular weight of 7,000 to 30,000, the composition ratio of lactic acid/glycolic acid being 80/10 to 100/0, and then subjecting said water-in-oil emulsion to microencapsulation.

SUMMARY OF THE INVENTION

According to the present invention, there is provided the microcapsules designed for zero order release of a physiologically active polypeptide over a period of at least two months.

DETAILED DESCRIPTION OF THE INVENTION

The physiologically active peptides usable in practice of this invention include those comprising with two or more amino acid residues and having a molecular weight of about 200 to about 100,000.

Examples of said peptides include luteinizing hormone-releasing hormone (LH-RH) and its analogs, for example, substances having LH-RH like activity [cf. U.S. Pat. Nos. 3,853,837, 4,008,209, 3,972,859 and 4,234,571, British Patent No. 1,423,083, Proceedings of the National Academy of Sciences of the United States of America, Volume 78, pages 6509–6512 (1981)] and LH-RH antagonists (cf. U.S. Pat. Nos. 4,086,219, 4,124,577, 4,253,997 and 4,317,815). There may be further mentioned prolactin, adrenocorticatropic hormone (ACTH), melanocyte-stimulating hormone (MSH), thyrotropin-releasing hormone (TRH), salts and derivatives thereof (cf. Toku-Kai Sho 50-121273, 51-116465), thyroid-stimulating hormone (TSH), lutenizing hormone (LH), follicle-stimulating hormone (FSH), vasopressin, vasopressin derivatives (desmopressin, etc.), oxytocin, calcitonin, parathyroid hormone (PTH) and its derivatives (cf. Toku-Kai Sho 62-28799), glucagon, gastrin, vasoactive intestinal peptide (VIP), lipocortin, vasocortin, atrial natriuretic peptide (ANP), endothelin, secretin, pancreozymin, cholecystokinin, angiotensin, human placental lactogen, human chorionic gonadotropin (HCG), enkephalin, enkephalin derivatives [cf. U.S. Pat. No. 4,382,923, E. P. Appln. Pub. No. 31,567], endorphin, kyotorphin, insulin, somatostatin, somatostatin derivatives (cf. U.S. Pat. Nos. 4,087,390, 4,093,574, 4,100,117 and 4253,998), growth hormones, and various cell proliferation differentiation factors [e.g. insulin-like growth factor (IGF), epidermal growth factor (EGF), fibroblast growth factor (FGF), platelet-derived growth factor (PDGF), nerve growth factor (NGF), hepatic cell growth factor (HGF), transformed growth factor (TGF-β), bone morphogenetic factor (BMF), vascularization factor, vascularization inhibiting factor, fibronectin, laminine, etc.], interferons (α-, β- and τ-type), interleukins (I, II, III, IV, V, VI and VII), tuftsin, thymopoietin, thymosin, thymostimulin, thymic humoral factor (THF), serum thymic factor (FTS) and derivatives thereof (cf. U.S. Pat. No. 4,229,438), and other thymic factors [cf. Proc. Natl. Acad. Sci. U.S.A., Vol. 78, pages 1162–1166 (1984)], tumor necrosis factor (TNF), colony stimulating factor (CSF), motilin, erythropoietin (EPO), dynorphin, bombesin, neurotensin, cerulein, bradykinin, urokinase, prourokinase, tissue plasminogen activator (t-PA), and derivatives thereof (cf. "Therapeutic Peptides and Proteins". Cold Spring Harbor Laboratory, New York, pp. 69–74, 1989), streptokinase, asparaginase, kallikrein, substance P., blood coagulation factors VIII and IX, lysozyme chloride, polymixin B, colistin, gramicidin, bacitracin, etc.

Especially, in a microcapsule comprising, as the physiologically active polypeptide, an analog of LH-RH, which is water-solube and has a molecular weight of 1,000 or more, [e.g. TAP-144 expressed by (pyr)Glu-His-Trp-Ser-Tyr-D-Leu-Leu-Arg-ProNHC$_2$H$_5$, or LHRH antagonist expressed by (pyr)Glu-His-Trp-Ser-Tyr-Trp-Leu-Arg-Pro-GlyNHC$_2$H$_5$], continuous sustained release is performed advantageously over a prolonged period of time.

These physiologically active peptides are used in amounts selected largely depending on the kind of peptide, desired pharmacological effects and duration of the effects, among others, and the amount ranges from about 0.01 mg to 5 g, more preferably, from 0.1 mg to 2 g, as the dosage of microcapsules. The concentration in a microcapsule depends on the physico-chemical properties of the drug, and it is selected within the range of about 0.01% to about 50% (w/w), more preferably within the range of 0.1% to 30% (w/w).

The concentration of said polypeptide in the inner aqueous phase of a microcapsule ranges from about 20% to 70% (w/w), preferably 25 to 65% (w/w), more preferably 35 to 60% (w/w) while it depends on its physico-chemical properties such as the solubility in water.

Examples of the polymer used as a release-controlling substance include copolymers or homopolymers of lactic acid/glycolic acid which have an acid residue in the molecule, are hardly soluble or insoluble in water and are biocompatible. The ratio of lactic acid/glycolic acid depends on the period required for sustained release, and is selected from the range of 100/0 to 80/20, preferably 100/0 to 90/10, more preferably 100/0.

As lactic acid, L-, D-and DL-lactic acid can be used, especially a copolymer or homopolymer prepared by polymerization of the monomer or oligomer of DL-lactic acid is advantageously utilized.

As the copolymer or homopolymer consisting of DL-lactic acid/glycolic acid, such polymers containing substantially no catalyst as obtained by polymerization in the absence of catalyst are advantageously used (cf. Toku-Kai Sho 61-285215). Polymers having a dispersion degree (ratio of weight-average molecular weight to number-average molecular weight) of 1.5 to 3.0, especially 1.5 to 2.5 are preferable.

The length of the period of continuous sustained release of microcapsules of this invention largely depends on the molecular weight of a polymer and the composition ratio of lactic acid/glycolic acid. In the case of preparing, for example, microcapsules performing continuous zero order release for at least three months, when the composition ratio of lactic acid/glycolic acid is 100/0, the preferable average-weight molecular weight of a polymer ranges from 7,000 to 25,000; when 90/10, from 7,000 to 30,000; and when 80/20, from 12,000 to 30,000.

In the present specification, the weight-average molecular weight and the degree of dispersion mean values which are determined by means of a gel-permeation chromatography using commercially available polystyrene of standard molecular weight.

The concentration of a polymer in the oil phase when preparing microcapsules is selected from the range of about 0.5 to 90% (w/w), more preferably from the range of about 2 to 60% (w/w).

The solution (oil phase) containing the above-mentioned polymer is that of the polymer dissolved in an organic solvent.

Said organic solvent may be any organic solvent which has a boiling point not higher than about 120° C. and hardly miscible with water. Examples are halogenated alkanes (e.g. dichloromethane, chloroform, chloroethane, trichloroethane, carbon tetrachloride, etc.), ethyl acetate, ethyl ether, benzene, toluene, etc. These may be used in admixture of two or more.

In the present invention, desirable microcapsules showing less initial release can be prepared without adding a drug retaining substance, but said retaining substance may be supplemented according to the situation. The drug retaining substance mentioned above is a compound which gives increased viscosity to the inner aqueous phase or solidifies by the action of temperature, addition of ions, or a compound having a basic residual group having protonic charge, which has interaction with a polymer to increase the viscosity of a W/O emulsion.

Examples of said drug retaining substance include gelatin, agar, alginic acid, polyvinyl alcohol, or a basic amino acid such as arginine, lysine, etc., a polypeptide containing a basic amino acid, an organic base such as N-methyl glucamine, and a natural or synthetic basic polymer.

These compounds can be used singly or as a mixture of two or more of them. While the amount of these compounds to be used depends on their kinds, it is preferable to have the concentration in the inner aqueous phase selected from the amount ranging from about 0.05% to 90% (w/w), more preferably from about 0.1% to 80% (w/w).

As conventional methods of controlling the releasability of these microcapsules, mention is made of a method of changing the hydrolysis rate [Biomaterials Vol. 5, 237–240 (1984)] and a method comprising incorporation of a water-soluble compound into matrix of microcapsules to create aqueous channels for releasing the drug. However, the former tends to invite shortening of a long-term of release, and the latter induces only an initial burst, thus an approximate zero-order release can hardly be expected, [Chem. Pharm. Bull. Vol. 36(4) 1502–1507 (1988)]. And, in the latter case, there is a fear of occurrence of undesirable side effects due to the increase of drug in blood at the initial stage. Further, there is also a known method (Toku-Kai Sho 57-150609), which comprises having the polymerization ratio of lactic acid/glycolic acid of PLGA to improve the time of suspending the release. This method is, however, directed to increase the speed of decomposition of the polymer, which, naturally, shortens the period of the release, thus there is a limit in realizing continuous release for a long period of time.

The sustained-release microcapsules of the present invention are prepared by, for example, the following method.

Stating more concretely, first, a physiologically active peptide is added to water in an amount required for realizing the above-mentioned concentration, to which is further added, when necessary, a drug-retaining substance such as the above-mentioned gelatin or basic amino acid to make a solution or a suspension having the above-mentioned concentration, to prepare the inner aqueous phase.

To this inner aqueous phase, there may be added a pH-adjusting agent for maintaining the stability or solubility of the physiologically active peptide, such as carbonic acid, acetic acid, oxalic acid, citric acid, phosphoric acid, hydrochloric acid, sodium hydroxide, arginine, lysine and their salts. And, there may further be added, as a stabilizer of the physiologically active peptide, albumin, gelatin, citric acid, sodium ethylenediamine tetraacetate, dextrin, sodium hydrogen sulfite or a polyol compound such as polyethylene glycol, or, as a preservative, there may be added conventionally usable ones, such as a para-hydroxybenzoic acid ester (e.g. methylparaben, propylparaben), benzyl alcohol, chlorobutanol or thimerosal.

The thus-obtained inner aqueous phase is added to a polymer-containing solution (oil phase), followed by an emulsification procedure to give a W/O type emulsion.

For said emulsification procedure, a known method of effecting dispersion is employed. As the method, mention is made of, for example, the intermittent shaking method, the method using a mixer such as a propeller-shaped stirrer, a turbine-shaped stirrer or the like, the colloid mill method, the homogenizer method or the ultrasonification method.

Then, the thus-prepared W/O emulsion is subjected to microencapsulation. An in-water drying or phase-separation method may be employed as a means of microencapsulation. In the case of preparing microcapsules by the in-water drying, said W/O emulsion is further added to a third aqueous phase to give a W/O/W ternary emulsion and, thereafter, the solvent in the oil phase is evaporated off to give microcapsules.

To the external aqueous phase, there may be added an emulsifying agent. As the emulsifying agent, there may be used any one capable of forming generally a stable O/W emulsion, for example an anionic surfactant (e.g. sodium oleate, sodium stearate, sodium lauryl sulfate, etc.), a non-ionic surfactant (e.g. polyoxyethylenesorbitan fatty acid ester (Tween 80, Tween 60, products of Atlas Powder Co.), a polyoxyethylene castor oil derivative (HCO-60, HCO-50, products of Nikko Chemicals), etc.), polyvinyl pyrrolidone, polyvinyl alcohol, carboxymethylcellulose, lecithin or gelatin. Such emulsifiers may be used either alone or in combination. The emulsifying agent concentration may suitably be selected within the range of about 0.01% to 20%, preferably within the range of about 0.05% to 10%.

For evaporation of the solvent from the oil phase, any of the common methods in general use can be employed. The method is conducted by, for example, gradually reducing the pressure while stirring with a propeller-shaped stirrer or a magnetic stirrer, or by using a rotary evaporator while adjusting the degree of vacuum. In this case, the required time can be reduced by gradually warming the W/O/W emulsion after the progress of solidification of the polymer to a certain extent for rendering the solvent removal more complete.

The thus-produced microcapsules are collected by centrifugation or filtration, rinsed several times with distilled water to thereby remove the free physiologically active peptide, drug retaining substance and the emulsifying agent adhering to the microcapsule surface, followed by dispersing the resultant microcapsules in e.g. distilled water and by freeze-drying, which is, if necessary, warmed under reduced pressure to thereby remove the moisture in the microcapsules and the solvent in the microcapsule wall more completely.

In the case of preparing microcapsules by the phase-separation method, a coacervation agent is gradually added to the said W/O emulsion under stirring to allow the polymer to precipitate and solidify.

A coacervation agent may be any solvent-miscible polymeric, mineral oil or vegetable oil compounds as exemplified by silicone oil, sesame oil, soybean oil, corn oil, cotton seed oil, coconut oil, linseed oil, mineral oils, n-hetane, n-heptane etc. These may be used as a mixture of two or more of them.

The microcapsules obtained thus above were collected by filtration and washed with, for example, heptane, repeatedly to remove the solvent of the polymer. Further, removal of the free drug and separation of the solvent were conducted in a manner similar to the in-water drying process. For preventing aggregation of microcapsules to one another during the washing, an agent for preventing aggregation may be added.

The microcapsules of the present invention designed for sustained-release produced by the above-mentioned in-water drying process more preferably perform a stable sustained-release for a long period of time.

Dosage forms of administering microcapsules for the present invention include injections, implantations and agents absorbed through mucous membrane of rectum or uterus.

The microcapsules obtained in the above manner are sieved, when necessary after slightly crushing, to eliminate excessively large microcapsules. The average grain size of microcapsules is within the range from about 0.5 to 1000 $\mu$m, desirably and preferably within the range of about 2 to 500 $\mu$m. When the microcapsules are used as injections in the form of suspension, the grain size may be sufficient so long as it satisfies the requirements for dispersability and injectability, for example, desirably within the range of about 2 to 100 $\mu$m.

The microcapsules produced by the methods according to this invention have many advantages. For instance, they scarcely undergo aggregation or cohesion to one another during the production step. There can be obtained microcapsules which are satisfactorily spherical in shape having an optional size. The step of removing the solvent from the oil phase is easy to control, whereby the surface structure of microcapsules, which is decisive for the rate of drug release can be controlled.

The microcapsules produced by the method of this invention can be easily administered as injections and implants intramuscularly, subcutaneously, intravenously, or at an organ, joint cavity or at a lesion such as tumors. They may also be administered in various dosage forms and thus can be used as materials in preparing such dosage forms.

For instance, in making up the microcapsules according to this invention for an injection, the microcapsules according to the invention are dispersed in an aqueous medium together with a dispersing agent (e.g. Tween 80, HCO-60, carboxymethylcellulose, sodium alginate, etc.), a preservative (e.g. methylparaben, propylparaben, etc.), an isotonizing agent (e.g. sodium chloride, mannitol, sorbitol, glucose, etc.), or suspended in an aqueous medium together with a vegetable oil such as sesame oil or corn oil. Such dispersion or suspension is formulated into a practically usable sustained-release injection.

Furthermore, the above microencapsulated sustained-release injection can be converted to a more stable, sustained-release injection by adding an additional excipient (e.g. mannitol, sorbitol, lactose, glucose, etc.), redispersing the resulting mixture and effecting solidification by freeze-drying or spray drying with extemporaneous addition of distilled water for injection or some appropriate dispersing agent.

The dose of the sustained-release preparation according to this invention may vary depending on the kind and amount of the physiologically active peptide, which is the active ingredient, dosage form, duration or drug release, recipient animal (e.g. warm-blooded animals such as mouse, rat, rabbit, sheep, pig, cow, horse, human) and purpose of administration but should be within the range of effective dose of said active ingredient. For example, the single dose per said animal of the microcapsules can adequately be selected within the range of about 0.1 mg to 100 mg/kg body weight, preferably about 0.2 mg to 50 mg/kg body weight.

In this manner, there is obtained a pharmaceutical composition prepared in the form of microcapsules which comprises an effective but greater amount of the physiologically active peptide as compared with the ordinary single dose and a biocompatible polymer and is capable of releasing the drug continuously over a prolonged period of time.

The sustained-release preparation according to the present invention has the following characteristics, among others: (1) Continuous sustained-release of the physiologically active peptide can be attained in various dosage forms. In particular, where a long-term treatment with an injection is required, the desired therapeutic effects can be achieved in a stable manner by injection of the preparation once in three month, or once in six months, instead of daily administration. Thus, said preparation can achieve a sustained drug release over a longer period as compared with the conventional sustained-release preparations. (2) When the preparation in which a biodegradable polymer is used is administered in the form of an injection, such surgical operation as implantation is no more required but the preparation can be administered subcutaneously, intramuscularly, or at an organ or a lesion, with ease in quite the same manner as the ordinary suspension injections. And, there is no need for taking the matrix out from the body after completion of the drug release.

The following Reference Example and Examples illustrate the invention in further detail.

REFERENCE EXAMPLE 1

A four-necked flask equipped with a thermometer, a condenser and an inlet of nitrogen was charged with 160 g of a 85% aqueous solution of DL-lactic acid. The solution was heated under reduced pressure for six hours in nitrogen streams at inner temperatures and pressures ranging from 105° C. and 350 mmHg to 150° C. and 30 mmHg to remove water thus distilled. The reaction was allowed to proceed at 175° C. for 90 hours under reduced pressure of 3 to 5 mmHg, and was then cooled to room temperatures to give 98 g of a substantially colorless massive polymer. This polymer was dissolved in tetrahydrofuran and the weight-average molecular weight and the degree of dispersion were determined by means of a gel-permeation chromatography using commercially available polystyrene of standard molecular weight to find 17,200 and 1.89, respectively.

EXAMPLE 1

TAP-144 (400 mg) was dissolved in 0.5 ml of distilled water to give an aqueous phase. The aqueous solution was added to a solution of 4 g of poly-DL-lactic acid [Lot No. 870818, weight-average molecular weight 18,000 (microcapsule Lot No. 244, 245) and Lot No. 880622, weight-average molecular weight 18,200, dispersity 1.76 (microcapsule Lot No. 248)] in 7.5 ml of dichloromethane. The mixture was stirred in a small-size homogenizer (Polytron, product of Kinematica, Switzerland) for about 60 seconds to give a W/O emulsion. This emulsion was cooled to 15° C. This emulsion was then poured into 1,000 ml of a 0.25% aqueous solution (previously cooled at 15° C.) of polyvinyl alcohol (PVA) which was stirred using a small-size homogenizer to give a W/O/W emulsion. Thereafter, dichloromethane was evaporated off, while stirring the W/O/W emulsion, to thereby solidify the inner W/O emulsion, followed by collecting thus solidified material by centrifugation.

The material was again dispersed in distilled water, which was subjected to centrifugation, followed by washing the drug and the dispersant then liberated.

Microcapsules thus collected were subjected to freeze-drying to remove the solvent and to dehydrate more completely to give powdery product. The content of the drug to be taken up in the microcapsules (Lot. 244, 245, 248) was prescribed as 9%, and the entrapped ratio was 100% or more.

These microcapsules were administered to rats (n=5) subcutaneously, then the TAP-144 remaining in the microcapsules at the injection site was determined quantitatively to measure the in vivo release rate of the drug. The results are shown in Table-1.

TABLE 1

| | in-vivo release-rate | | | | |
|---|---|---|---|---|---|
| | Amount of Drug Remaining Subcutaneously (%) | | | | |
| Lot | 1 day | 2 weeks | 4 weeks | 8 weeks | 14 weeks |
| 244 | 102.2 | 89.0 | 70.2 | 44.0 | 9.5 |
| 245 | 105.9 | 82.4 | 69.4 | 52.1 | 9.8 |
| 248 | 104.1 | 75.4 | 72.8 | 43.7 | 11.6 |

These microcapsules do not show initial burst and continuous release of TAP-144 was observed for 14 weeks, i.e. longer than 3 months, with substantially good reproducibility.

EXAMPLE 2

Similarly, TAP-144 (400 mg) was dissolved in 0.5 ml of distilled water to give an aqueous phase. Four grams of poly-DL-lactic acid having a weight-average molecular weight of 8,400 (Lot. 870304, microcapsule Lot. 312) was dissolved in 5 ml of dichloromethane to give an oil phase. The aqueous phase and the oil phase were mixed in the same manner as described above to give a W/O emulsion.

This emulsion was cooled to 13° C., and then poured into 1,000 ml of 0.25% aqueous solution of polyvinyl alcohol (PVA). The mixture was processed in the same manner as described above to give a W/O/W emulsion, which was prepared into microcapsules.

Further, 550 mg of TAP-144 was dissolved in 1 ml of distilled water. On the other hand, 4 g each of three samples of poly-DL-lactic acid (Lot No. 890717, molecular weight 14,100, dispersity 2.00 microcapsule Lot. 402; Lot No. 890720, molecular weight 17,200, dispersity 1.89, microcapsule Lot No. 405; Lot No. 890721, molecular weight: 17,500, dispersity: 1.87, microcapsule Lot No. 406) was dissolved in 7.5 ml each of dichloromethane. The above aqueous solution was added to each of the three samples dissolved in dichloromethane, followed by processing in the same manner as above to give three samples of W/O emulsion. The respective emulsions were poured into 1,000 ml each of three samples of 0.25% aqueous solution of polyvinyl alcohol previously cooled at 15° C. (the first one) and at 18° C. (the second and third ones), which were respectively processed in the same manner as described in the foregoing to obtain microcapsules. The entrapped ratios of the drug were 101%, 113% and 103%, respectively.

Table-2 shows in vivo release rates of the drug in the respective microcapsules measured in the same manner as described above.

TABLE 2

| Lot | n | Amount of Drug Remaining Subcutaneously (%) | | | | |
|---|---|---|---|---|---|---|
| | | 1 day | 1 week | 2 weeks | 8 weeks | 12 weeks | 14 weeks |
| 312 | 5 | 86.3 | 82.2 | 41.2 | 9.8 | — | — |
| 402 | 3 | 98.0 | 78.2 | 64.9 | 38.4 | 20.0 | — |
| 405 | 5 | 88.8 | 79.4 | 52.2 | 33.8 | — | 21.3 |
| 406 | 5 | 85.5 | 86.2 | 56.7 | 38.8 | — | 23.1 |

The release of the drug, after a small amount of initial release, shows a continuous long release over longer than two months. The term of release was dependent upon the hydrolysis rate of the high molecular polymer then employed.

EXAMPLE 3

Microcapsules were prepared, in the same manner as in Example 1, from an aqueous phase prepared by dissolving 400 mg of TAP-144 in 0.5 ml of distilled water and an oil phase prepared by dissolving 4 g of polylactic acid-glycolic acid (90/10) [Lot No. 870320 (weight-average molecular weight : 19,000), microcapsule Lot No. 315, Lot No.; 891020 (weight-average molecular weight: 13,800), microcapsule Lot No. 410]. Referring to the microcapsule Lot No. 410, an aqueous solution prepared by dissolving 550 mg of TAP-144 in 1 ml of distilled water was used as the inner aqueous phase, and the temperatures of the W/O emulsion, and the external phase were adjusted to 15° C. and 18° C., respectively. The entrapped ratios of the drug in these microcapsules were 106% and 100%, respectively.

These microcapsules were administered to rats subcutaneously in the same manner as described above, and their in vivo release rates of the drug were evaluated. Table-3 shows that sustained-release microcapsules for a continuous prolonged period over more than two months were obtained.

TABLE 3

| Lot | Amount of Drug Remaining Subcutaneously (%) | | | | | |
|---|---|---|---|---|---|---|
| | 1 day | 1 week | 2 weeks | 4 weeks | 6 weeks | 8 weeks | 10 weeks |
| 315 | 77.4 | 76.0 | 59.2 | 51.6 | 41.1 | 25.8 | — |
| 410 | 93.5 | 88.3 | 64.1 | 52.5 | 33.1 | 32.7 | 15.4 |

EXAMPLE 4

Microcapsules were prepared, in the same manner as Example 1, from an aqueous phase prepared by dissolving 280 mg of TRH (free form) in 0.25 ml of distilled water and an oil phase prepared by dissolving, in 6 ml of dichloromethane, poly-DL-lactic acid (average molecular weight 17,200, dispersity 1.89) employed in Example 2, and by adjusting the temperature of the W/O emulsion and external aqueous phase at 15° C. The entrapped ratio of the drug in the microcapsules thus obtained (Lot No. R-103) was 85.8%.

Table-4 shows that the release of the drug in thus-obtained microcapsule was as long-lasting as covering about 3 months.

TABLE 4

| Lot | Amount of Drug Remaining Subcutaneously (%) | | | | |
|---|---|---|---|---|---|
| | 1 day | 2 weeks | 4 weeks | 8 weeks | 12 weeks |
| R103 | 98.3 | 80.0 | 61.8 | 30.6 | 6.7 |

What we claim is:

1. A microcapsule exhibiting zero order release of luteinizing hormone-releasing hormone (LH-RH) analog for a period of at least two months upon administration, which is produced by preparing a water-in-oil emulsion comprising an inner aqueous phase free from a drug retaining substance containing 35 to 60% (W/W) of the LH-RH analog, and an oil phase containing a homopolymer of lactic acid or a copolymer of lactic acid and glycolic acid with a ratio of lactic acid/glycolic acid of 100/0 to 90/10, the homo-or copolymer having a weight-average molecular weight of 13,800 to 19,000 and a dispersion degree (ratio of weight-average molecular weight to number average molecular weight) of 1.5 to 2.5, as the material for forming an outer wall of the microcapsule; and then subjecting said water-in-oil emulsion to microencapsulation.

2. A microcapsule according to claim 1, which exhibits zero order release for a period of at least three months upon administration.

3. A microcapsule according to claim 1, wherein the concentration of the copolymer or homopolymer in the oil phase is from 2 to 60% by weight.

4. A microcapsule according to claim 1, wherein the LH-RH analog is water-soluble and has a molecular weight of 1,000 or more.

5. A process for preparing a microcapsule exhibiting zero order release of luteinizing hormone-releasing hormone (LH-RH) analog for a period of at least two months upon administration, which comprises preparing a water-in-oil emulsion comprising an inner aqueous phase free from a drug retaining substance containing 35 to 60% (W/W) of the LH-RH analog, and an oil phase containing a homopolymer of lactic acid or a copolymer of lactic acid and glycolic acid with a ratio of lactic acid/glycolic acid of 100/0 to 90/10, the homo-or copolymer having a weight-average molecular weight of 13,800 to 19,000 and a dispersion degree (ratio of weight-average molecular weight to number average molecular weight) of 1.5 to 2.5, as the material for forming an outer wall of the microcapsule, and then subjecting said water-in-oil emulsion to in-water drying or phase-separation.

6. A process according to claim 5, wherein the water-in-oil emulsion is dispersed in an aqueous phase and the resulting water/oil/water ternary emulsion is subjected to in-water drying.

7. A process according to claim 5, wherein the water-in-oil emulsion is dispersed in an aqueous phase containing polyvinyl alcohol as an emulsifying agent.

8. A process according to claim 5, wherein the LH-RH analog is water-soluble and has a molecular weight of 1,000 or more.

9. A process according to claim 5, wherein the LH-RH analog is (pyr)Glu-His-Trp-Ser-Tyr-D-Leu-Leu-Arg-ProNHC$_2$H$_5$.

10. A microcapsule according to claim 1, wherein the oil phase contains a homopolymer of lactic acid.

11. A microcapsule according to claim 1, wherein the oil phase contains a homopolymer of lactic acid having a weight-average molecular weight of 14,100 to 18,200 or a lactic acid/glycolic acid copolymer with a ratio of lactic acid/glycolic acid of 100/0 to 90/10 that has a weight-average molecular weight of from 13,800 to 19,000.

12. A microcapsule according to claim 1, wherein the oil phase contains a lactic acid/glycolic acid copolymer with a ratio of lactic acid/glycolic acid of 100/0 to 90/10.

13. A microcapsule according to claim 1, wherein the oil phase contains a lactic acid/glycolic acid copolymer with a ratio of lactic acid/glycolic acid of 100/0 to 90/10 that has a weight-average molecular weight of from 13,800 to 19,000.

14. A process according to claim 5, wherein the oil phase contains a homopolymer of lactic acid.

15. A process according to claim 5, wherein the oil phase contains a homopolymer of lactic acid having a weight-average molecular weight of 14,100 to 18,200, or a lactic acid/glycolic acid copolymer with a ratio of lactic acid/glycolic acid of 100/0 to 90/10 that has a weight-average molecular weight of from 13,800 to 19,000.

16. A process according to claim 5, wherein the oil phase contains a lactic acid/glycolic acid copolymer with a ratio of lactic acid/glycolic acid of 100/0 to 90/10.

17. A process according to claim 5, wherein the oil phase contains a lactic acid/glycolic acid copolymer with a ratio of lactic acid/glycolic acid of 100/0 to 90/10 that has a weight-average molecular weight of from 13,800 to 19,000.

* * * * *